United States Patent
Zhao

(10) Patent No.: US 11,771,644 B1
(45) Date of Patent: Oct. 3, 2023

(54) WHITENING TOOTHPASTE CAPABLE OF EFFECTIVELY REMOVING DENTAL PLAQUE AND TARTAR

(71) Applicant: Zhejiang Airsun Commodity Co., Ltd., Yiwu (CN)

(72) Inventor: Guosheng Zhao, Yiwu (CN)

(73) Assignee: ZHEJIANG AIRSUN COMMODITY CO., LTD., Yiwu (CN)

( * ) Notice: Subject to any disclaimer, the term of this patent is extended or adjusted under 35 U.S.C. 154(b) by 0 days.

(21) Appl. No.: 18/133,529

(22) Filed: Apr. 12, 2023

(30) Foreign Application Priority Data

Jul. 6, 2022 (CN) .......................... 202210787786.0

(51) Int. Cl.
| | | |
|---|---|---|
| A61K 8/9789 | (2017.01) | |
| A61K 8/46 | (2006.01) | |
| A61K 8/21 | (2006.01) | |
| A61K 8/24 | (2006.01) | |
| A61K 8/73 | (2006.01) | |
| A61Q 11/00 | (2006.01) | |
| A61K 8/99 | (2017.01) | |
| A61K 8/25 | (2006.01) | |

(52) U.S. Cl.
CPC .............. *A61K 8/9789* (2017.08); *A61K 8/21* (2013.01); *A61K 8/24* (2013.01); *A61K 8/25* (2013.01); *A61K 8/463* (2013.01); *A61K 8/731* (2013.01); *A61K 8/99* (2013.01); *A61Q 11/00* (2013.01); *A61K 2236/15* (2013.01); *A61K 2236/19* (2013.01); *A61K 2236/333* (2013.01); *A61K 2236/39* (2013.01); *A61K 2236/53* (2013.01)

(58) Field of Classification Search
CPC .. A61K 35/74; A61K 6/00; A61P 1/02; C12N 1/20; A61Q 11/00
USPC ............................... 424/49, 50, 52
IPC ....................................... A61Q 11/00
See application file for complete search history.

(56) References Cited

U.S. PATENT DOCUMENTS

| | | | | |
|---|---|---|---|---|
| 2008/0118444 | A1* | 5/2008 | Hsu ......... | A61Q 11/00 424/50 |
| 2010/0254915 | A1* | 10/2010 | Kao ......... | A61Q 11/00 424/49 |

FOREIGN PATENT DOCUMENTS

| | | | | |
|---|---|---|---|---|
| CN | 101991516 | A | 3/2011 | |
| CN | 104586644 | A | 5/2015 | |
| CN | 107690330 | A | 2/2018 | |
| CN | 108338361 | A | 7/2018 | |
| CN | 109890378 | A | 6/2019 | |
| CN | 110623911 | A | 12/2019 | |
| CN | 111631975 | A | 9/2020 | |
| CN | 112089670 | A | 12/2020 | |
| CN | 113288856 | A | 8/2021 | |
| EP | 1498039 | * | 3/2005 | ............... A23L 1/28 |
| KR | 101666348 | B1 | 10/2016 | |
| WO | WO 2008/045579 | * | 4/2008 | ............ A01N 65/00 |

\* cited by examiner

*Primary Examiner* — Walter E Webb
(74) *Attorney, Agent, or Firm* — Bayramoglu Law Offices LLC

(57) ABSTRACT

A whitening toothpaste capable of effectively removing dental plaque and tartar includes cinnamic acid extract, osthole extract, *Lactobacillus salivarius* fermentation broth, glycerol, sorbitol, propylene glycol, silicon dioxide, sodium carboxymethyl cellulose, sodium lauryl sulfate, sodium fluoride, potassium fluoride or sodium monofluorophosphate and mint powder. In the present invention, the cinnamon and osthole extracting solutions and *Lactobacillus salivarius* are selected and used for bacteriostatic, tartar removing and whitening effects, fluoride additives are used for removing pigmentation, and dental plaque in a matched manner, and in combination with a toothpaste system, the toothpaste capable of effectively removing dental plaque and tartar is prepared.

12 Claims, 2 Drawing Sheets

WHITENING TOOTHPASTE CAPABLE OF EFFECTIVELY REMOVING DENTAL PLAQUE AND TARTAR

CROSS REFERENCE TO THE RELATED APPLICATIONS

This application is based upon and claims priority to Chinese Patent Application No. 202210787786.0, filed on Jul. 6, 2022, the entire contents of which are incorporated herein by reference.

TECHNICAL FIELD

The present invention belongs to the field of cleaning products, particularly relates to toothpaste, and especially relates to whitening toothpaste capable of effectively removing dental plaque and tartar.

BACKGROUND

Nowadays society advocates nature and health, and people pay much attention to the safety and efficacy of products. The same is true for oral care products. Plant herbs have the advantages of small side effects and high safety, and have become the mainstream of market consumption. Most of the components of toothpaste are friction agents, the function of toothpaste is mainly as an intermediary, which acts between a toothbrush and teeth, enhances the friction between toothbrush and teeth, and urges toothbrush to clean teeth. Dental plaque is an adhesive plaque film formed by bacteria in the oral cavity adhering to the surfaces of teeth and accumulating over time. Tartar is what we often call yellow tartar, those dirty things attached to the surfaces of teeth. Tartar, also known as bacterial plaque, is a biological film gradually deposited on the surfaces of teeth. The bacteria in tartar are mainly streptococcus, anaerobic bacteria, etc. existing in normal oral cavity. After the tartar accumulates to a certain thickness, the bacteria inside it close to surfaces of teeth begin to transfer to anaerobic respiration because they are isolated from the air. The acid produced by anaerobic respiration here can not be washed away by saliva in time, therefore it will corrode the mineral components in enamel and further promote the formation of dental caries. The tartar accumulated at the roots of the teeth can also stimulate the gums, leading to periodontal diseases such as periodontitis. In daily life, black or yellow dental plaque appears on teeth, which is mostly caused by pigmentation on the surfaces of teeth, and is common in people who have the habit of drinking strong tea or coffee and smokers. The main role of toothpaste is played by the friction agent in it, and teeth are cleaned by rubbing surfaces of teeth with the toothbrush. However, ordinary toothpaste on the market does not contain chemical components that can decompose the pigment on surfaces of teeth, such that it is difficult to realize the long-cherished wish of consumers to completely remove dental plaque by brushing teeth. In addition, many people have retching when brushing teeth. Apart from the symptoms of pharyngolaryngitis, it actually has something to do with the toothpaste they choose. If the mouth is not rinse thoroughly after brushing teeth, toothpaste residues are ingested, which causes local gastroenteritis, then troubles people's lives.

*Cinnamomum cassia*, a plant of Lauraceae, is an evergreen tree, which is common in tropical regions and some subtropical regions. The cinnamon resources in China rank first in the world. Moreover, cinnamon has been used as traditional Chinese medicine for more than 2000 years. According to the Guangxi Journal of Traditional Chinese Medicine, "cinnamon oil has the function of killing germs and viruses, and can be used as wind-expelling medicine and stomach-invigorating medicine for oral administration". It is recorded in Compendium of Materia Medica that cinnamon varieties are divided into two types according to different harvest seasons: spring cinnamon and autumn cinnamon. Cinnamon plants have good medical value in treating frostbite in winter, abdominal pain and diarrhea, cough and vomiting, dizziness and headache, physical weakness and stomach cold, etc., and cinnamaldehyde in cinnamon also has the advantages of antibacterial and antiseptic. In addition, modern pharmacological experiment studies show that osthole has the effects of anti-hypertension, anti-arrhythmia, anti-aging, anti-tumor, anti-osteoporosis, anti-inflammation and anti-allergy. Adding osthole-containing extract to toothpaste can play a certain role in anti-inflammation and dental plaque inhibition by traditional Chinese medicine, which facilitates oral health. Fluorine is an indispensable component in teeth and bones, and a small amount of fluorine can promote the resistance of tooth enamel to bacterial acid corrosion. After the free fluorine in toothpaste comes into contact with tooth enamel, fluorapatite is produced which makes teeth hard, thus playing the role of anti-acid dissolution and anti-caries, which is commonly called caries prevention. Toothpaste with fluoride can also inhibit the acid production of oral bacteria, and change the environment suitable for oral bacteria to live, thus playing the role of caries prevention and dental plaque removal.

Therefore, the cinnamon and osthole extracting solutions are selected and used as bacteriostatic and tartar removing agent, and can play a certain whitening effect matching the *Lactobacillus salivarius* fermentation broth. In addition, pigmentation and dental plaque can be better removed matching fluoride additives, and in combination with a toothpaste system, whitening toothpaste capable of effectively removing dental plaque and tartar is prepared.

SUMMARY

In order to overcome the shortcomings in the prior art, the objective of the present invention is to provide toothpaste, which has the effects of tartar removing and whitening, and has a certain antibacterial effect in an oral cavity. The objective is realized by the following technical solution:

On the one hand, the present invention provides a composition capable of effectively removing dental plaque and tartar, the composition thereof includes cinnamic acid extract, osthole extract, *Lactobacillus salivarius* fermentation broth, glycerol, sorbitol, propylene glycol, silicon dioxide, sodium carboxymethyl cellulose, sodium lauryl sulfate, sodium fluoride, potassium fluoride or sodium monofluorophosphate and mint powder.

On the other hand, the present invention provides a preparation method for whitening toothpaste capable of effectively removing dental plaque and tartar. The preparation method thereof is as follows:

S1, preparing a cinnamon extracting solution with a steam distillation extraction method: weighing 200-300 g of dried cinnamon, performing grinding, then adding water over the material, performing pretreatment with an ultrasonic processor, ultrasonic pretreatment being conductive to break a cell wall of the cinnamon raw material and dissolve effective components, then adding 3-5 L of deionized water, and performing heating to keep the system in a boiling state for 2-5 h to obtain a cinnamon extract stock solution;

S2, preparing an osthole extracting solution: weighing 10-15 g of high-quality fruit of Fructus Cnidii of umbelliferae, performing grinding, decocting 3-5 g of Cnidium monnieri with 100-200 ml of water for 5 times for 30-50 min each time, combining filtrate, adding 60 ml of ethanol, performing standing for 8 h, removing precipitates to obtain filtrate, then volatilizing the ethanol with a rotary evaporator, adding water to a constant volume of 120 mL, adding 40 mL of glycerol into 55 mL of water, continuously performing extraction for 2 times, and taking a propylene glycol layer solution for later use;

S3, inoculating seeds of *Lactobacillus salivarius* in a fermentation tank according to inoculation amount of 3%, performing culture at constant temperature of 37° C., collecting fermentation broth cultured to a stable stage, and centrifuging the fermentation broth to remove bacteria after concentration of the bacteria in the fermentation broth reaches a certain concentration to obtain *Lactobacillus salivarius* fermentation broth;

S4, preparing liquid: adding 80-200 ml of cinnamon extract stock solution prepared in S1, 50-150 ml of osthole extracting solution prepared in S2, and 3-5 mL of *Lactobacillus salivarius* fermentation broth prepared in S3 into a vacuum paste maker, weighing appropriate amount of glycerol, sorbitol and propylene glycol into the vacuum paste maker, performing mixing and stirring for 20-40 min, and addition of these materials being capable of keeping degree of wetting and soft liquidity of paste to a certain extent;

S5, preparing powder: weighing 10-15 g of silicon dioxide, 20-25 g of sodium carboxymethyl cellulose, 8-10 g of sodium lauryl sulfate, and 0.3-0.8 g of sodium fluoride, potassium fluoride or sodium monofluorophosphate, and performing uniform mixing; the powder is one of the main components of the paste, which assists a toothbrush in cleaning teeth when brushing the teeth; and S6, mixing the liquid with the powder: adding the powder prepared in S5 into the vacuum paste maker to be mixed with the liquid prepared in S4, performing stirring for 30 min, then adding 3-5 g of mint powder, further, turning on a vacuum pump of the paste maker to start vacuumizing, after performing vacuum stirring for 30-50 min, turning off the vacuum pump and the vacuum paste maker to stop stirring, filling a hose with toothpaste, and sealing a tail with a self-made tail sealing machine.

Preferably: 200 g of cinnamon is weighed in S1;
Preferably: 15 g of fruit of F
ructus Cnidii and 3 g of indium monnieri are weighed in S2;
Preferably: 30 ml of glycerol, 50 ml of sorbitol and 10 ml of propylene glycol are selected and used in S4; and
Preferably: vacuum degree in S5 is kept at about –0.095 MPa.

Strains of *Lactobacillus salivarius* (JYLS-372) involved in the present invention are all purchased from Shaanxi Feimi Biotechnology Co., Ltd., and number of *Lactobacillus salivarius* is 10 billion cfu/g, and concentration of the bacteria in the fermentation broth is 3.0×109 cfu/mL.

1. The toothpaste prepared by the present invention has no hormones, no pigments, no synthetic spices, no preservatives and other harmful chemical additives, and is pure plant organic toothpaste.

2. The toothpaste prepared by the present invention uses the cinnamon and osthole extracting solutions to inhibit bacteria, and adds the *Lactobacillus salivarius* fermentation broth on this basis, the three components may achieve the maximum whitening effect in a specific proportion, and the toothpaste also has the advantages of non-toxicity, no irritation, sterilization and tooth cleaning.

3. The toothpaste prepared by the present invention is environmental friendliness, and the health is not affected even if the toothpaste is eaten by mistake when brushing teeth.

4. The present invention has simple operation and a low production cost, which facilitates mass production.

5. The toothpaste paste prepared by the present invention is delicate and smooth in paste, light yellow and translucent, with fine and rich foam, good taste, cool and refreshing smell and moderate viscosity.

DETAILED DESCRIPTION OF THE EMBODIMENTS

Figure 1:
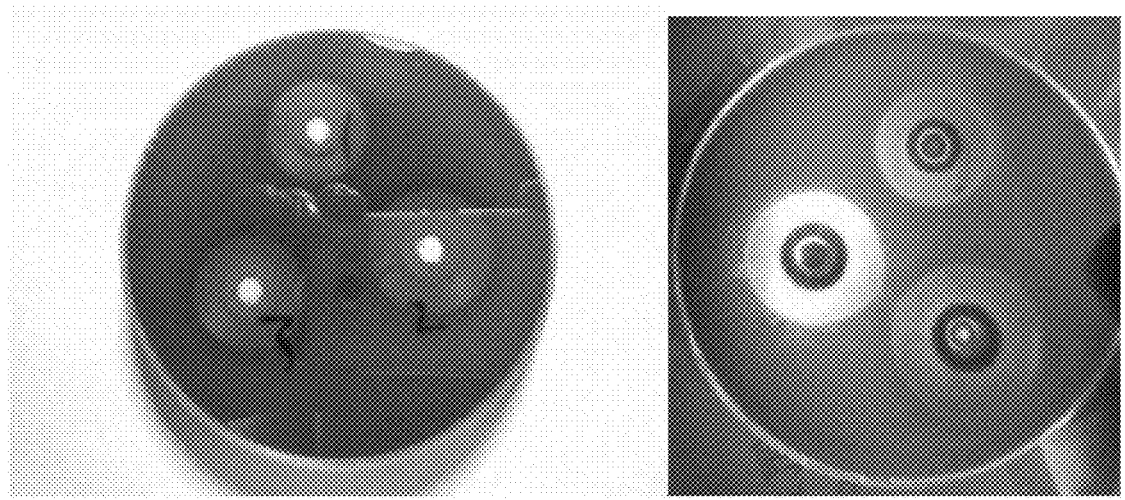
FIG. 1 is a diagram showing comparison results of antibacterial annulus of Example 2 and Comparative Example 3 in the present invention with those of commercially available toothpaste.

*Lactobacillus salivarius* used in the present example is purchased from Shaanxi Feimi Biotechnology Co., Ltd., and number of the *Lactobacillus salivarius* is 10 billion cfu/g.

Lactobacillus youth used in the present example is purchased from Shaanxi Feimi Biotechnology Co., Ltd., and number of the lactobacillus youth is 10 billion cfu/g.

Example 1

S1, 200 g of dried cinnamon was weighed, grinding was performed, then water over the material was added, pretreatment was performed with an ultrasonic processor, ultrasonic pretreatment was conductive to break a cell wall of the cinnamon raw material and dissolve effective components, then 3 L of deionized water was added, and heating was performed to keep the system in a boiling state for 2 h to obtain a cinnamon extract stock solution;

S2, an osthole extracting solution was prepared: 10 g of high-quality fruit of Fructus Cnidii of umbelliferae was weighed, grinding was performed, 3 g of Cnidium monnieri was decocted with 100 ml of water for 5 times for 30 min each time, filtrate was combined, 60 ml of ethanol was added, standing was performed for 8 h, precipitates were removed to obtain filtrate, then the ethanol was volatilized with a rotary evaporator, water was added to a constant volume of 120 mL, 40 mL of glycerol was added into 55 mL of water, extraction was continuously performed for 3 times, and a glycerol layer solution was taken for later use;

S3, seeds of *Lactobacillus salivarius* were inoculated in a fermentation tank according to inoculation amount of 3%, culture was performed at constant temperature of 37° C., fermentation broth cultured to a stable stage was collected, and the fermentation broth was centrifuged to remove bacteria after concentration of the bacteria in the fermentation broth was 3.0×109 CFU/mL to obtain *Lactobacillus salivarius* fermentation broth;

S4, liquid was prepared: 80 ml of cinnamon extracting solution prepared in S1, 50 ml of osthole extracting solution prepared in S2, and 3 mL of *Lactobacillus salivarius* fermentation broth prepared in S3 were added into a vacuum paste maker, appropriate amount of glycerol, sorbitol and propylene glycol were added into the vacuum paste maker, mixing and stirring were performed for 20 min;

S5, powder was prepared: 10 g of silicon dioxide, 20 g of sodium carboxymethyl cellulose, 8 g of sodium lauryl sulfate, and 0.3 g of sodium fluoride were weighed, and uniform mixing was performed;

S6, the liquid was mixed with the powder: the powder prepared in S5 was added into the vacuum paste maker to be mixed with the liquid prepared in S4, stirring was performed for 30 min, then 3 g of mint powder was added, further, a vacuum pump of the paste maker was turned on to start vacuumizing, after vacuum stirring was performed for 30 min, the vacuum pump and the vacuum paste maker were turned off to stop stirring, a hose was filled with toothpaste, and a tail was sealed with a self-made tail sealing machine.

In Comparative Example 1, except that the cinnamon extracting solution is not added in S3, other parameters are the same as in Example 1.

In Comparative Example 2, except that the osthole extracting solution is not added in S3, other parameters are the same as in Example 1.

The present invention selects *Staphylococcus aureus* (ATCC6538), *Escherichia coli* (ATCC25922), *Candida albicans* (ATCC10231), *Porphyromonas gingivalis* (ATCC33277) and *Streptococcus mutans* (ATCC700610) as test strains. With reference to article 7.3 of QB/T2738-2012, a bacteriostatic rate of the toothpaste diluted by 3 times and 90 times with deionized water is tested for 5 min, the test is repeated 5 times, and an average value is taken.

TABLE 1

| Example 1 | *Staphylococcus aureus* | *Escherichia coli* | *Candida albicans* | *Porphyromonas gingivalis* | *Streptococcus mutans* |
| --- | --- | --- | --- | --- | --- |
| Bacteriostatic rate of 4 times of dilution (%) | 99.85 ± 0.56 | 99.36 ± 0.23 | 99.41 ± 018 | 95.37 ± 1.31 | 99.12 ± 0.56 |
| Bacteriostatic rate of 90 times of dilution (%) | 99.25 ± 0.84 | 90.23 ± 123 | 60.36 ± 1.44 | 55.28 ± 87 | 60.61 ± 2.35 |

TABLE 2

| Comparative example 1 | *Staphylococcus aureus* | *Escherichia coli* | *Candida albicans* | *Porphyromonas gingivalis* | *Streptococcus mutans* |
| --- | --- | --- | --- | --- | --- |
| Bacteriostatic rate of 4 times of dilution (%) | 50.23 ± 1.82 | 60.34 ± 1.97 | 40.23 ± 0.89 | 20.12 ± 2.56 | 18.42 ± 1.30 |
| Bacteriostatic rate of 90 times of dilution (%) | 45.11 ± 0.81 | 9.184 ± 0.23 | 15.46 ± 0.52 | 8.11 ± 0.18 | 5.34 ± 0.07 |

TABLE 3

| Comparative example 1 | *Staphylococcus aureus* | *Escherichia coli* | *Candida albicans* | *Porphyromonas gingivalis* | *Streptococcus mutans* |
| --- | --- | --- | --- | --- | --- |
| Bacteriostatic rate of 4 times of dilution (%) | 65.23 ± 0.91 | 50.21 ± 0.54 | 35.87 ± 0.69 | 40.51 ± 0.27 | 22.36 ± 0.82 |
| Bacteriostatic rate of 90 times of dilution (%) | 23.47 ± 0.25 | 20.33 ± 0.44 | 15.32 ± 0.25 | 13.18 ± 0.74 | 10.12 ± 0.21 |

It may be seen from the results in Tables 1, 2 and 3 that the toothpaste prepared in Example 1, Comparative Example 1 and Comparative Example 2 has a bacteriostatic effect on the *Staphylococcus aureus*, the *Escherichia coli*, the *Candida albicans*, the *Porphyromonas gingivalis* and the *Streptococcus mutans* after being diluted by 4 times and 90 times, it shows that the toothpaste prepared in Example 1 has the best bacteriostatic effect, and by means of Comparative Examples 1 and 2, it also shows that the cinnamon and osthole extracting solutions have synergistic effect, and the cinnamon and osthole extracting solutions have better bacteriostatic effect. The reason may be that cinnamon contains a large number of active ingredients such as flavonoids, saponins and polysaccharides, which have certain antibacterial effects. However, osthole contains active ingredients such as bornyl isovalerate, which may interact with the active ingredients in the cinnamon, thus making the cinnamon have a better antibacterial effect.

Example 2

S1, a cinnamon extracting solution was prepared with a steam distillation extraction method: 300 g of dried cinnamon was weighed, grinding was performed, then water over the material was added, pretreatment was performed with an ultrasonic processor, ultrasonic pretreatment was conductive to break a cell wall of the cinnamon raw material and dissolve effective components, then 5 L of deionized water was added, and heating was performed to keep the system in a boiling state for 5 h to obtain a cinnamon extract stock solution;

S2, an osthole extracting solution was prepared: 15 g of high-quality fruit of Fructus Cnidii of umbelliferae was weighed, grinding was performed, 5 g of Cnidium monnieri was decocted with 200 ml of water for 5 times for 50 min each time, filtrate was combined, 60 ml of ethanol was added, standing was performed for 8 h, precipitates were removed to obtain filtrate, then the ethanol was volatilized with a rotary evaporator, water was added to a constant volume of 120 mL, 40 mL of glycerol was added into 55 mL of water, extraction was continuously performed for 3 times, and a glycerol layer solution was taken for later use;

S3, seeds of *Lactobacillus salivarius* were inoculated in a fermentation tank according to inoculation amount of 3%, culture was performed at constant temperature of 37° C., fermentation broth cultured to a stable stage was collected, and the fermentation broth was centrifuged to remove bacteria after concentration of the bacteria in the fermentation broth was $3.0 \times 10^9$ CFU/mL to obtain *Lactobacillus salivarius* fermentation broth;

S4, liquid was prepared: 200 ml of cinnamon extracting solution prepared in S1, 150 ml of osthole extracting solution prepared in S2, and 5 mL of *Lactobacillus salivarius* fermentation broth prepared in S3 were added into a vacuum paste maker, appropriate amount of glycerol, sorbitol and propylene glycol were added into the vacuum paste maker, mixing and stirring were performed for 40 min;

S5, powder was prepared: 15 g of silicon dioxide, 25 g of sodium carboxymethyl cellulose, 10 g of sodium lauryl sulfate, and 0.8 g of potassium fluoride were weighed, and uniform mixing was performed;

S6, the liquid was mixed with the powder: the powder prepared in S5 was added into the vacuum paste maker to be mixed with the liquid prepared in S4, stirring was performed for 30 min, then 5 g of mint powder was added, further, a vacuum pump of the paste maker was turned on to start vacuumizing, after vacuum stirring was performed for 50 min, the vacuum pump and the vacuum paste maker were turned off to stop stirring, a hose was filled with toothpaste, and a tail was sealed with a self-made tail sealing machine.

Figure 2:
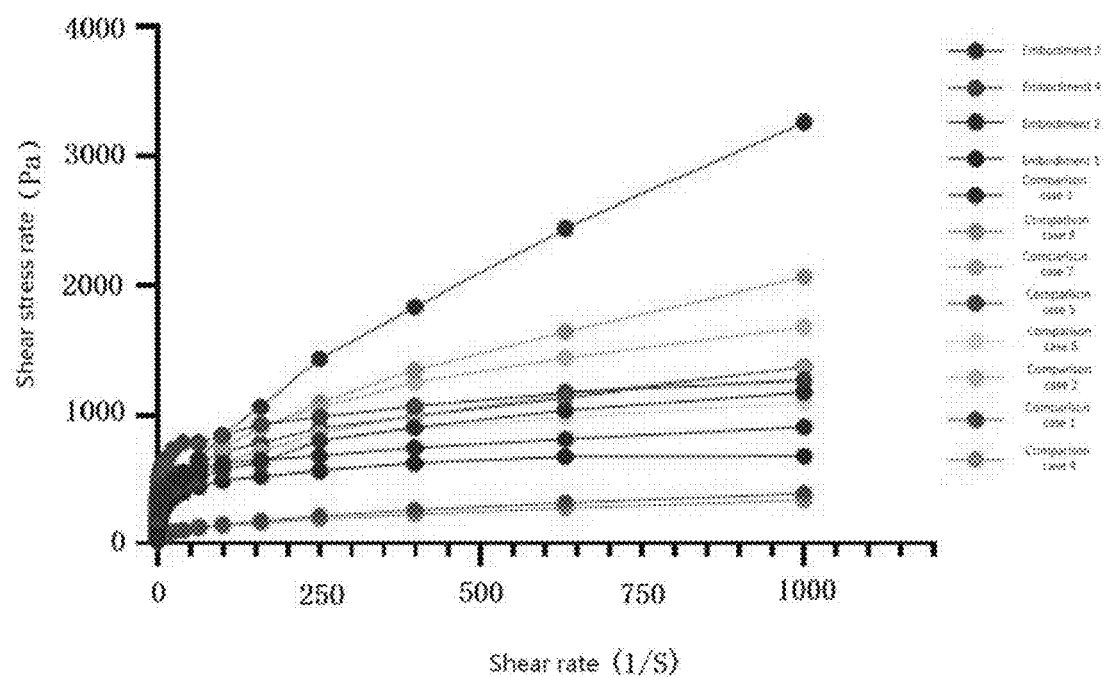
FIG. 2 is a flow curve of toothpaste prepared in Examples 1-3 and Comparative Examples 1-7 of the present invention.

In Comparative Example 3, except that the osthole extracting solution is not added in S3, other parameters are the same as in Example 2.

with reference to a test method for antibacterial annuli in Disinfection Technical Guidelines, antibacterial annulus tests for commercially available toothpaste (No. 1), toothpaste prepared in Example 2 (No. 2) and toothpaste prepared in Comparative Example 3 (No. 3) are performed, and experiments are performed in parallel for 5 times, and an average value is taken as the result. FIG. 2 is the experimental result of antibacterial annuli in the present invention, average diameters of antibacterial annuli of the toothpaste prepared in Example 2, the commercially available toothpaste and the toothpaste prepared in Comparative Example 3 is 21 mm, 18 mm and 4 mm in sequence. The diameter of the antibacterial annulus of the toothpaste prepared in Example 2 is obviously larger than that of the commercially available toothpaste, which shows that the toothpaste prepared in Example 2 has higher bacteriostatic activity than the commercially available toothpaste. Comparative Example 3 also has toothpaste with an antibacterial annulus having a diameter of 4 mm, which shows that the mint powder added in S5 has a certain bacteriostatic effect and may form a small antibacterial annulus.

Example 3

S1, a cinnamon extracting solution was prepared with a steam distillation extraction method: 230 g of dried cinnamon was weighed, grinding was performed, then water over the material was added, pretreatment was performed with an ultrasonic processor, ultrasonic pretreatment was conductive to break a cell wall of the cinnamon raw material and dissolve effective components, then 4 L of deionized water was added, and heating was performed to keep the system in a boiling state for 3 h to obtain a cinnamon extract stock solution;

S2, an osthole extracting solution was prepared: 13 g of high-quality fruit of Fructus Cnidii of umbelliferae was weighed, grinding was performed, 4 g of Cnidium monnieri was decocted with 120 ml of water for 5 times for 40 min each time, filtrate was combined, 60 ml of ethanol was added, standing was performed for 8 h, precipitates were removed to obtain filtrate, then the ethanol was volatilized with a rotary evaporator, water was added to a constant volume of 120 mL, 40 mL of glycerol was added into 55 mL of water, extraction was continuously performed for 3 times, and a glycerol layer solution was taken for later use;

S3, seeds of *Lactobacillus salivarius* were inoculated in a fermentation tank according to inoculation amount of 3%, culture was performed at constant temperature of 37° C., fermentation broth cultured to a stable stage was collected, and the fermentation broth was centrifuged to remove bacteria after concentration of the bacteria in the fermentation broth was $3.0 \times 10^9$ CFU/mL to obtain *Lactobacillus salivarius* fermentation broth;

S4, liquid was prepared: 150 ml of cinnamon extracting solution prepared in S1, 80 ml of osthole extracting solution prepared in S2, and 5 mL of *Lactobacillus salivarius* fermentation broth prepared in S3 were added into a vacuum paste maker, appropriate amount of glycerol, sorbitol and propylene glycol were added into the vacuum paste maker, mixing and stirring were performed for 30 min;

S5, powder was prepared: 13 g of silicon dioxide, 22 g of sodium carboxymethyl cellulose, 9 g of sodium lauryl sulfate, and 0.6 g of sodium monofluorophosphate were weighed, and uniform mixing was performed;

S6, the liquid was mixed with the powder: the powder prepared in S5 was added into the vacuum paste maker to be mixed with the liquid prepared in S4, stirring was performed for 30 min, then 4 g of mint powder was added, further, a vacuum pump of the paste maker was turned on to start vacuumizing, after vacuum stirring was performed for 38 min, the vacuum pump and the vacuum paste maker were turned off to stop stirring, a hose was filled with toothpaste, and a tail was sealed with a self-made tail sealing machine.

In Comparative Example 4, except that the sodium carboxymethyl cellulose is not added in S4, other parameters are the same as in Example 3.

In Comparative Example 5, except that the sodium lauryl sulfate is not added in S4, other parameters are the same as in Example 3.

In Comparative Example 6, except that the silicon dioxide is not added in S4, other parameters are the same as in Example 3.

In Comparative Example 7, except that the sodium monofluorophosphate is not added in S4, other parameters are the same as in Example 3.

A flow curve and a viscosity curve reflect flow characteristics of the toothpaste at different shear rates, which determines performance of the toothpaste in preparation, filling and use. The toothpaste is required to have excellent shear thinning characteristics, manifested as pseudoplastic fluid, the better pseudoplasticity, the easier transportation, better stability and more convenient use in a production process.

Figure 3:
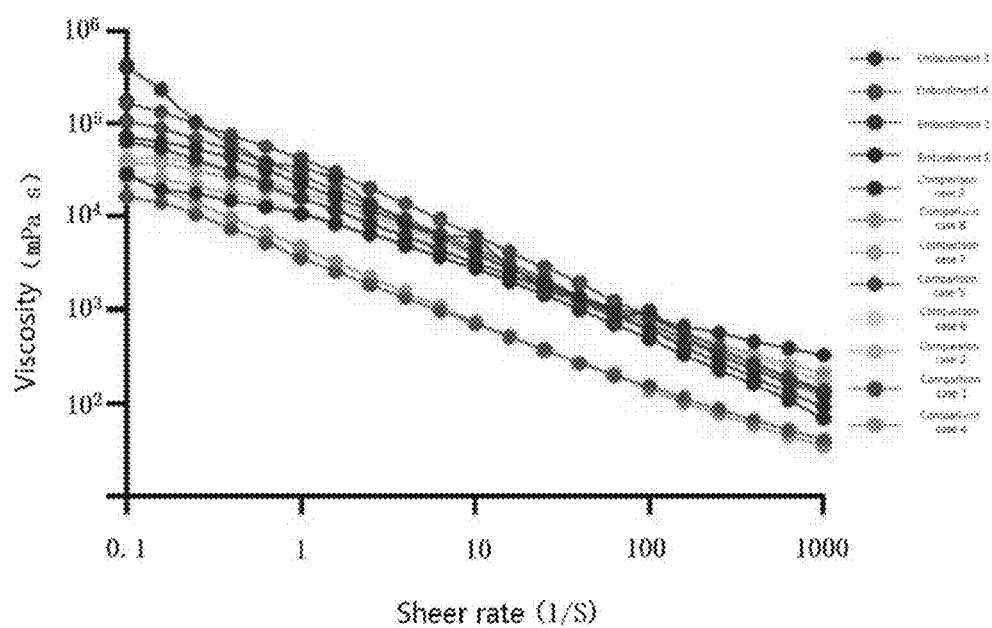
FIG. 3 is a viscosity curve of the toothpaste prepared in Examples 1-3 and Comparative Examples 1-7 of the present invention.

FIGS. 2 and 3 are the flow curve and viscosity curve of the toothpastes prepared in Examples 1-3 and Comparative Examples 1-7 of the present invention, by means of comparative analysis, it may be seen that all the prepared toothpaste show the rheological characteristics of pseudoplastic fluid, and viscosity gradually decreases with increase of the shear rate, that is, shear thinning. Under shearing action, a three-dimensional network structure in the toothpaste breaks in the direction of shearing action, which makes irregular particles originally suspended in the system be provided in a flow direction, and chain molecules are unwound, stretched and oriented in a driving force direction, which causes the decrease of apparent viscosity.

Example 4

S1, a cinnamon extracting solution was prepared with a steam distillation extraction method: 250 g of dried cinnamon was weighed, grinding was performed, then water over the material was added, pretreatment was performed with an ultrasonic processor, ultrasonic pretreatment was conductive to break a cell wall of the cinnamon raw material and dissolve effective components, then 4.5 L of deionized water was added, and heating was performed to keep the system in a boiling state for 4 h to obtain a cinnamon extract stock solution;

S2, an osthole extracting solution was prepared: 14 g of high-quality fruit of Fructus Cnidii of umbelliferae was weighed, grinding was performed, 4 g of Cnidium monnieri was decocted with 140 ml of water for 5 times for 44 min each time, filtrate was combined, 60 ml of ethanol was added, standing was performed for 8 h, precipitates were removed to obtain filtrate, then the ethanol was volatilized with a rotary evaporator, water was added to a constant volume of 120 mL, 40 mL of glycerol was added into 55 mL of water, extraction was continuously performed for 3 times, and a glycerol layer solution was taken for later use;

S3, seeds of *Lactobacillus salivarius* were inoculated in a fermentation tank according to inoculation amount of 3%, culture was performed at constant temperature of 37° C., fermentation broth cultured to a stable stage was collected, and the fermentation broth was centrifuged to remove bacteria after concentration of the bacteria in the fermentation broth was 3.0×109 CFU/mL to obtain *Lactobacillus salivarius* fermentation broth;

S4, liquid was prepared: 180 ml of cinnamon extracting solution prepared in S1, 110 ml of osthole extracting solution prepared in S2, and 5 mL of *Lactobacillus salivarius* fermentation broth prepared in S3 were added into a vacuum paste maker, appropriate amount of glycerol, sorbitol and propylene glycol were added into the vacuum paste maker, mixing and stirring were performed for 34 min;

S5, powder was prepared: 14 g of silicon dioxide, 24 g of sodium carboxymethyl cellulose, 9 g of sodium lauryl sulfate, and 0.4 g of sodium monofluorophosphate were weighed, and uniform mixing was performed;

S6, the liquid was mixed with the powder: the powder prepared in S5 was added into the vacuum paste maker to be mixed with the liquid prepared in S4, stirring was performed for 30 min, then 4.4 g of mint powder was added, further, a vacuum pump of the paste maker was turned on to start vacuumizing, after vacuum stirring was performed for 40 min, the vacuum pump and the vacuum paste maker were turned off to stop stirring, a hose was filled with toothpaste, and a tail was sealed with a self-made tail sealing machine.

In Comparative Example 8, except that the sodium monofluorophosphate is not added in S4, other parameters are the same as in Example 4.

In Comparative Example 9, except that the *Lactobacillus salivarius* fermentation broth is not added in S4, other parameters are the same as in Example 1.

In Comparative Example 10, except that the *Lactobacillus salivarius* fermentation broth is replaced with lactobacillus youth fermentation broth in S4, other parameters are the same as in Example 1.

Experiments show that the use of toothpaste with fluoride may reduce probability of oral diseases. Appropriate use of the toothpaste with fluoride by teenagers and the elderly is good for teeth. The biggest difference between the present invention and ordinary toothpaste lies in addition of bactericidal cinnamon and osthole extracting solutions, which has a bactericidal effect and may relieve the oral diseases to a certain extent, and the advantages of the present invention may be better brought into play by combining trace fluorine doping with plant additives.

A detection method and judgment basis for soluble fluorine and free fluorine involved in the present invention are the methods provided in the national standard Toothpaste (GB/8372-2017) for detection.

TABLE 4

| Toothpaste | Fluorine-containing species | Content range (%) | Standard requirements (%) |
| --- | --- | --- | --- |
| Example 3 | Soluble fluorine | 0.01-0.03 | 0.05-0.15 |
|  | Free fluorine | 0.02-0.05 | 0.05-0.15 |
| Example 4 | Soluble fluorine | 0.03-0.05 | 0.05-0.15 |
|  | Free fluorine | 0.02-0.04 | 0.05-0.15 |

TABLE 4-continued

| Toothpaste | Fluorine-containing species | Content range (%) | Standard requirements (%) |
|---|---|---|---|
| Comparative example 7 | Soluble fluorine Free fluorine | 0 0 | 0.05-0.15 0.05-0.15 |
| Comparative example 8 | Soluble fluorine Free fluorine | 0 0 | 0.05-0.15 0.05-0.15 |

Whitening Effect Test
1. Test samples: toothpaste prepared in Examples 1-4 and Comparative Examples 1-2 and 9-10 and whitening toothpaste on the market;
2. Experimental process:
  2.1 Test objects: 270 volunteers aged 30-50 with exogenous tooth stains are selected, and randomly divided into 9 groups with 30 people in each group;
  2.2 Test method: All volunteers are given the same soft toothbrush, and use the test samples for brushing teeth separately, once in the morning and once in the evening, for two minutes each time, and the volunteers are required to keep other usual oral hygiene habits, daily diet, smoking and other habits. Clinical examination is performed at baseline, the fourth week and the eighth week, and is completed by the same examiner. Data are statistically analyzed by T-test, two-sided test is performed, and a test level a is 0.05, with the results seen in Table 5.
  2.3 Evaluation method: Tooth stains are evaluated by Lobene stain index, and the size and degree of stains are evaluated by the number of 0-3.
Lobene Stain Index Grading Score:
0: no stain exists;
1: the stains do not exceed ⅓ of surfaces of teeth, and the stains are mild (yellow or yellowish brown);
2: the stains do not exceed ⅔ of the surfaces of the teeth, and the stains are moderate (moderate brown); and
3: the stains exceed ⅔ of the surfaces of the teeth, and the stains are severe (dark brown or black).
3. Test results: see Table 5 for specific test results.

TABLE 5

| | | Stain index | | |
|---|---|---|---|---|
| Group | n | Baseline | Fourth week | Eighth week |
| Example 1 group | 30 | 2.87 ± 0.51 | 2.34 ± 0.84 | 1.84 ± 0.56 |
| Example 2 group | 30 | 2.86 ± 0.49 | 2.45 ± 0.78 | 2.26 ± 0.81 |
| Example 3 group | 30 | 2.88 ± 0.64 | 2.51 ± 0.99 | 2.24 ± 0.68 |
| Example 4 group | 30 | 2.87 ± 0.56 | 2.36 ± 0.87 | 2.05 ± 1.02 |
| Comparative Example 1 group | 30 | 2.85 ± 0.52 | 2.80 ± 0.79 | 2.75 ± 0.77 |
| Comparative Example 2 group | 30 | 2.88 ± 0.55 | 2.79 ± 0.58 | 2.75 ± 0.57 |
| Comparative Example 9 group | 30 | 2.95 ± 0.88 | 2.93 ± 1.32 | 2.87 ± 0.97 |
| Comparative Example 10 group | 30 | 2.93 ± 0.68 | 2.85 ± 1.11 | 2.81 ± 0.81 |
| Ordinary toothpaste control group | 30 | 2.93 ± 0.79 | 2.45 ± 0.58 | 2.13 ± 0.88 |

It may be seen from Table 5 that the toothpaste prepared in Examples 1-4 of the present invention has a remarkable tooth whitening effect, especially, the whitening effect in Example 1 is the best, and therefore Example 1 is the best example of the present invention. However, in Comparative Examples 1-2 and 9, the cinnamon extracting solution, the osthole extracting solution and *Lactobacillus salivarius* are removed separately, which causes significantly reduced whitening effect; however, in Comparative Example 10, the whitening effect of the samples is not improved after the *Lactobacillus salivarius* fermentation broth is replaced with lactobacillus youth fermentation broth, which shows that not all probiotics may match the cinnamon and osthole extracting solutions to achieve the whitening effect, and also shows that the three have a certain synergistic effect and may achieve antibacterial, tartar removing and whitening effects. However, the whitening effect in Example 1 is the best, which shows that the synergistic effect of the three is the largest under the proportion in Example 1.

The above examples are merely used for expressing specific embodiments of the present invention, their descriptions are specific and detailed, but they cannot be interpreted as limiting the scope of protection of the present invention. It should be noted that any other variations, modifications, substitutions, combinations and simplifications made without departing from the spirit essence and principles of the present invention are equivalent substitutions to those of ordinary skill in the art, and will fall within the scope of protection of the present invention.

What is claimed is:
1. A preparation method for a whitening toothpaste capable of effectively removing a dental plaque and a tartar, comprising:
  S1, weighing a dried cinnamon, performing grinding, then adding water over a resulting material, performing pretreatment with an ultrasonic processor, then adding deionized water, and performing heating to keep a resulting system in a boiling state to obtain a cinnamon extract stock solution;
  S2, weighing Fructus Cnidii, performing grinding, decocting Cnidium monnieri with water for 5 times for 30-50 min each time, combining a first resulting filtrate, adding ethanol, performing standing, removing precipitates to obtain a second resulting filtrate, then volatilizing the ethanol with a rotary evaporator, adding water to a constant volume of 120 mL to obtain a resulting mixture, adding 40 mL of glycerol into 55 mL of the resulting mixture, continuously performing extraction for 3 times, and taking a glycerol layer solution for later use to obtain a Fructus Cnidii and Cnidium monnieri extracting solution;
  S3, inoculating a seed solution of *Lactobacillus salivarius* in a fermentation tank according to an inoculation amount of 3%, performing culture at a constant temperature of 37° C., collecting a fermentation broth cultured to a stable stage, and centrifuging the fermentation broth to remove bacteria after a concentration of the bacteria in the fermentation broth reaches a certain concentration to obtain a *Lactobacillus salivarius* fermentation broth;
  S4, adding 80-200 ml of the cinnamon extract stock solution prepared in S1, 50-150 ml of the Fructus Cnidii and Cnidium monnieri extracting solution prepared in S2, and 3-5 mL of the *Lactobacillus salivarius* fermentation broth prepared in S3 into a vacuum paste maker, weighing an appropriate amount of glycerol, sorbitol, and propylene glycol into the vacuum paste maker, and performing mixing and stirring for 20-40 min to obtain a resulting liquid;
  S5, weighing 10-15 g of silicon dioxide, 20-25 g of sodium carboxymethyl cellulose, 8-10 g of sodium lauryl sulfate, and 0.3-0.8 g of sodium fluoride, potas- sium fluoride, or sodium monofluorophosphate, and performing uniform mixing to obtain a resulting powder; and S6, adding the resulting powder prepared in S5 into the vacuum paste maker to be mixed with the resulting liquid prepared in S4, performing stirring for 30 min, then adding 3-5 g of a mint powder, further, turning on a vacuum pump of the vacuum paste maker to start vacuumizing, after performing a vacuum stirring for 30-50 min, turning off the vacuum pump and the vacuum paste maker to stop the vacuum stirring, filling a hose with the whitening toothpaste, and sealing a tail with a self-made tail sealing machine.

2. The preparation method for the whitening toothpaste capable of effectively removing the dental plaque and the tartar according to claim 1, wherein 200-300 g of cinnamon is weighed in S1.

3. The preparation method for the whitening toothpaste capable of effectively removing the dental plaque and the tartar according to claim 1, wherein 10-15 g of Fructus Cnidii is weighed in S2.

4. The preparation method for the whitening toothpaste capable of effectively removing the dental plaque and the tartar according to claim 1, wherein 3-5 g of Cnidium monnieri is weighed in S2.

5. The preparation method for the whitening toothpaste capable of effectively removing the dental plaque and the tartar according to claim 1, wherein the concentration of the bacteria in the fermentation broth in S3 reaches $2.0 \times 10^9$-$3.0 \times 10^9$ cfu/mL.

6. The preparation method for the whitening toothpaste capable of effectively removing the dental plaque and the tartar according to claim 1, wherein 30-50 ml of glycerol, 50-65 ml of sorbitol, and 5-10 ml of propylene glycol are selected and used in S4.

7. A toothpaste prepared by the preparation method according to claim 1.

8. The toothpaste according to claim 7, wherein 200-300 g of cinnamon is weighed in S1.

9. The toothpaste according to claim 7, wherein 10-15 g of Fructus Cnidii is weighed in S2.

10. The toothpaste according to claim 7, wherein 3-5 g of Cnidium monnieri is weighed in S2.

11. The toothpaste according to claim 7, wherein the concentration of the bacteria in the fermentation broth in S3 reaches $2.0 \times 10^9$-$3.0 \times 10^9$ cfu/mL.

12. The toothpaste according to claim 7, wherein 30-50 ml of glycerol, 50-65 ml of sorbitol, and 5-10 ml of propylene glycol are selected and used in S4.

* * * * *